(12) United States Patent
Campbell et al.

(10) Patent No.: US 8,101,545 B2
(45) Date of Patent: Jan. 24, 2012

(54) COATING COMPOSITIONS FOR MARKING SUBSTRATES

(75) Inventors: Jonathan Campbell, Riehen (CH); John Whitworth, Manchester (GB); Alan Platt, Manchester (GB); Ian Street, Manchester (GB)

(73) Assignee: Datalase Ltd., Widness, Cheshire (GB)

( * ) Notice: Subject to any disclaimer, the term of this patent is extended or adjusted under 35 U.S.C. 154(b) by 947 days.

(21) Appl. No.: 11/886,137

(22) PCT Filed: Mar. 13, 2006

(86) PCT No.: PCT/EP2006/060658
§ 371 (c)(1),
(2), (4) Date: Apr. 21, 2008

(87) PCT Pub. No.: WO2006/108745
PCT Pub. Date: Oct. 19, 2006

(65) Prior Publication Data
US 2009/0071367 A1 Mar. 19, 2009

(30) Foreign Application Priority Data
Mar. 23, 2005 (EP) .................................. 05102337

(51) Int. Cl.
*B41M 5/333* (2006.01)
*B41M 5/337* (2006.01)
*C09D 11/00* (2006.01)

(52) U.S. Cl. ..................... 503/201; 106/31.17; 427/150; 503/209; 503/216

(58) Field of Classification Search .................. None
See application file for complete search history.

(56) References Cited

U.S. PATENT DOCUMENTS

| | | | |
|---|---|---|---|
| 3,373,170 A | 3/1968 | Jones | 260/345.8 |
| 4,916,247 A | 4/1990 | Steinmann | 556/82 |
| 5,256,805 A | 10/1993 | O'Lenick, Jr. | 554/39 |
| 2006/0040217 A1 | 2/2006 | Stubbs | 430/363 |

FOREIGN PATENT DOCUMENTS

| | | |
|---|---|---|
| JP | 3-76873 | 3/1991 |
| JP | 11-67604 | 11/1999 |
| WO | 2004/043704 | 5/2004 |

OTHER PUBLICATIONS

Derwent AN 1999-238901[20] of JP 11-67604.
Derwent AN 1990-241627[32] of JP 3-76873.

*Primary Examiner* — Bruce H Hess
(74) *Attorney, Agent, or Firm* — Stoel Rives LLP

(57) ABSTRACT

The present invention provides coating compositions for marking substrates, which comprises a color former, an amine salt of an organic metal compound, a binder, a solvent, and optionally additional components, wherein the amine salt of the organic metal compound is of formula (I) in which X is silicon or boron, and E and F are the same or different and are selected from the group consisting of a, b, c, d, e, f, g, h in which $R^6$ and $R^7$ are the same or different are hydrogen, $C_{1-4}$-alkyl, $C_{1-4}$-alkoxy, halogen, amino or carboxy, and for X=silicon o=1 and p=0, and $R^1$ is aryl, aralkyl or $C_{1-4}$-alkyl, or o=1 and p=1, and $R^1$ and $R^2$ together form a one residue selected from the group consisting of a, b, c, d, e, f, g and h, and for X=boron o=0 and p=0, and $R^3$, $R^4$ and $R^5$ are the same or different and are hydrogen, $C_{1-12}$-alkyl, $C_{1-6}$-hydroxyalkyl, allyl, aralkyl or arylsulfonyl, in which aralkyl or arylsulfonyl can be substituted with $C_{1-4}$-alkyl, or $R^3$ and $R^4$ together with the nitrogen to which they are attached form a morpholino or piperidino ring. The present invention also provides a process for the preparation of the composition of the present invention, substrates coated with these compositions, a process for preparing coated substrates, a process for preparing a marked substrate using these compositions, a marked substrate obtainable by the latter process and amine salts of the organic metal compounds of formula I.

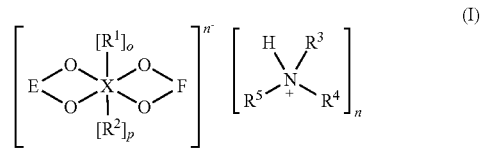

(I)

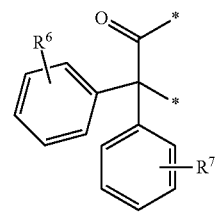

a

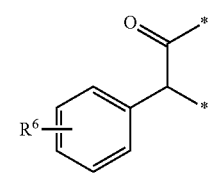

b c

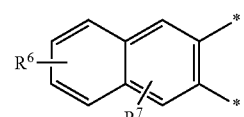

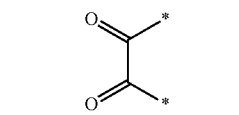

d e

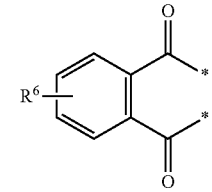

f

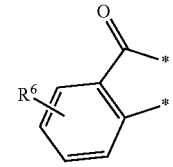

16 Claims, No Drawings

COATING COMPOSITIONS FOR MARKING SUBSTRATES

The present invention refers to coating compositions for marking substrates, to a process for the preparation of these compositions, to substrates coated with these compositions and to a process for their preparation, to a process for preparing marked substrates using these compositions and marked substrate obtainable by the latter process and to amine salts of the organic metal compounds.

Packaging usually needs to be marked with visible information such as logos, bar codes, expiry dates or batch numbers. One way to achieve this is by coating the packaging with a composition comprising a colour former and a colour developer, which upon treatment with energy such as heat reacts to form a visible colour.

WO 02/074548 describes coating compositions comprising an oxyanion of a multivalent metal, for example ammonium octamolybdate (AOM), a binder, which is typically polymeric, and a solvent such as water or ethanol. These compositions were coated on a substrate, for example carton board, dried to yield an opaque coating and exposed to an IR laser to produce a black image.

The disadvantage of the coating composition of WO 02/074548 is that only opaque coatings and black images can be obtained.

WO 2004/043704 describes coating compositions comprising a colour former, an amine compound of molybdenum, tungsten or vanadium, an organic solvent and optionally a polymeric binder. An example of an "amine molybdate" is bis(2-ethylhexyl)amine octamolybdate. The compositions were coated on substrates such as polyethylene terephthalate film, aluminium foil or polypropylene packaging film, dried to yield an opaque or transparent coating and exposed to an IR laser or thermal printer to produce a coloured image.

There is an ongoing need to develop further coating compositions.

It is an object of the present invention to provide coating compositions, which yield coloured images of excellent intensity and of high durability especially in terms of water resistance and abrasion resistance, and which coating compositions can be modulated in order to achieve either transparent or opaque coatings.

These objects are solved by the coating composition according to claim 1, the substrates according to claims 11 and 15, the processes according to claims 10, 12 and 13, and by amine salts of organic metal compounds according to claim 16.

The compositions of the present invention comprise a colour former, an amine salt of an organic metal compound, a binder, a solvent, and optionally additional components, wherein the amine salt of the organic metal compound is of formula

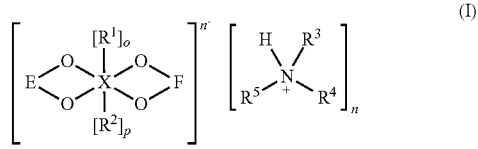 (I)

in which X is silicon or boron, and
E and F are the same or different and are selected from the group consisting of

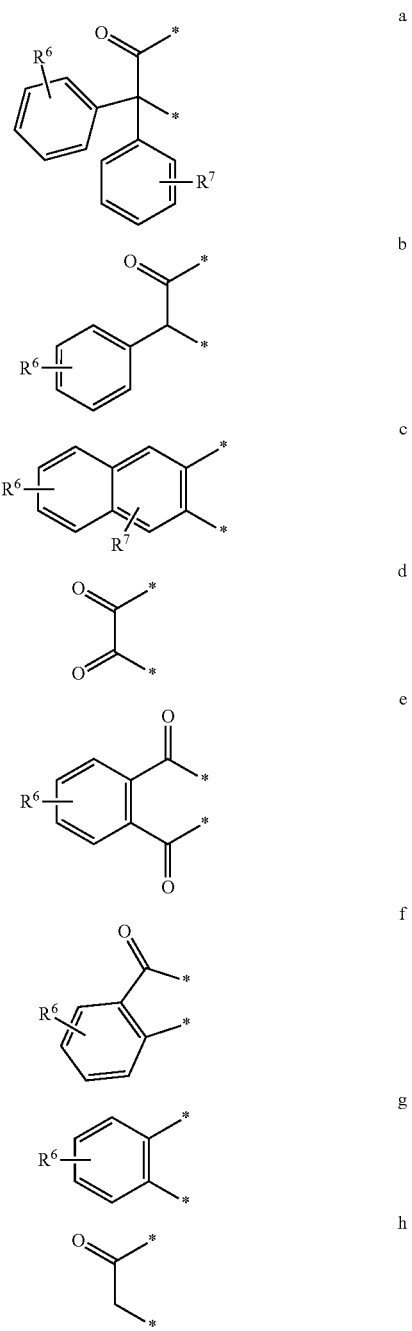

in which $R^6$ and $R^7$ are the same or different are hydrogen, $C_{1-4}$-alkyl, $C_{1-4}$-alkoxy, halogen, amino or carboxy, and
for X=silicon o=1 and p=0, and $R^1$ is aryl, aralkyl or $C_{1-4}$-alkyl, or
  o=1 and p=1, and $R^1$ and $R^2$ together form a one residue selected from the group consisting of a, b, c, d, e, f, g and h, and
for X=boron o=0 and p=0, and
$R^3$, $R^4$ and $R^5$ are the same or different and are hydrogen, $C_{1-12}$-alkyl, $C_{1-6}$-hydroxyalkyl, allyl, aralkyl or arylsulfonyl, in which aralkyl or arylsulfonyl can be substituted with $C_{1-4}$-alkyl, or $R^3$ and $R^4$ together with the nitrogen to which they are attached form a morpholino or piperidino ring.

Examples for $C_{1-4}$-alkyl are methyl, ethyl, propyl, isopropyl, butyl, sec-butyl, isobutyl and tert-butyl. Examples for $C_{1-4}$-alkoxy are methoxy, ethoxy, propoxy, isopropoxy, butoxy, sec-butyoxy, isobutoxy and tert-butoxy. Examples of halogen are chlorine, bromine, fluorine and iodine. Examples of aryl are phenyl, 1-naphthyl, 2-naphthyl and pyridyl. Examples of aralkyl are benzyl and 2-phenylethyl. Examples of $C_{1-12}$-alkyl are methyl, ethyl, propyl, isopropyl, butyl, sec-butyl, isobutyl and tert-butyl, pentyl, hexyl, heptyl, octyl, 2-ethylhexyl, nonyl, decyl, undecyl and dodecyl. Examples of $C_{1-6}$-hydroxyalkyl are hydroxymethyl, 2-hydroxyethyl, 2-hydroxypropyl, 3-hydroxypropyl, 4-hydroxybutyl, 5-hydroxypentyl and 6-hydroxyhexyl. Examples of arylsulfonyl are phenylsulfonyl and tosyl.

In preferred compositions of the present invention, in which X is silicon,
E and F are the same or different and are selected from the group consisting of

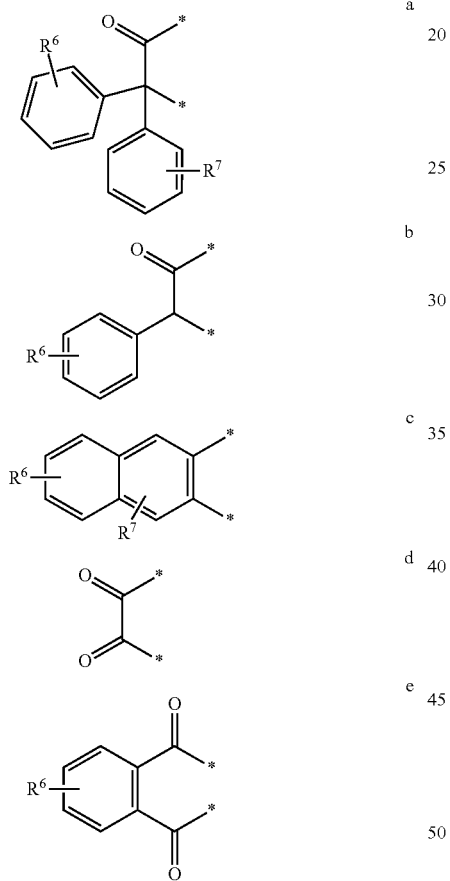

a b c d e in which $R^6$ and $R^7$ are the same or different are hydrogen, $C_{1-4}$-alkyl, $C_{1-4}$-alkoxy, halogen, amino or carboxy, and
o=1 and p=0 and $R^1$ is aryl, aralkyl or $C_{1-4}$-alkyl, or
o=1 and p=1, and $R^1$ and $R^2$ together form one residue selected from the group consisting of a, b, c, d and e, and
$R^3$, $R^4$ and $R^5$ are the same or different and are hydrogen, $C_{1-12}$-alkyl, $C_{1-6}$-hydroxyalkyl, allyl, aralkyl or arylsulfonyl, in which aralkyl or arylsulfonyl can be substituted with $C_{1-4}$-alkyl, or $R^3$ and $R^4$ together with the nitrogen to which they are attached form a morpholino or piperidino ring.

In more preferred compositions of the present invention, in which X is silicon,
E and F are the same or different and are selected from the group consisting of

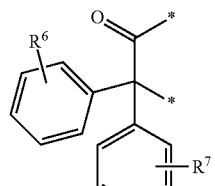

a

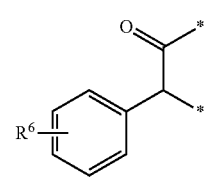

b

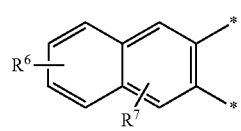

c

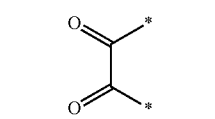

d

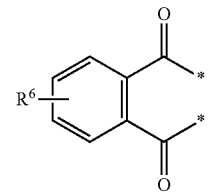

e in which $R^6$ and $R^7$ are the same or different and are hydrogen or $C_{1-4}$-alkyl,
o=1 and p=0, and $R^1$ is aryl,
o=1 and p=1, and $R^1$ and $R^2$ together form a one residue selected from the group consisting of a, b, c, d and e, and
$R^3$, $R^4$ and $R^5$ are the same or different and are hydrogen, $C_{1-10}$-alkyl, $C_{1-6}$-hydroxyalkyl, allyl, or arylsulfonyl, in which arylsulfonyl can be substituted with $C_{1-4}$-alkyl, or $R^3$ and $R^4$ can together with the nitrogen to which they are attached form a morpholino or piperidino ring.

Examples of $C_{1-10}$-alkyl are methyl, ethyl, propyl, isopropyl, butyl, sec-butyl, isobutyl and tert-butyl, pentyl, hexyl, heptyl, octyl, 2-ethylhexyl, nonyl and decyl.

In most preferred compositions of the present invention, in which X is silicon,
E and F are the same and are selected from the group consisting of

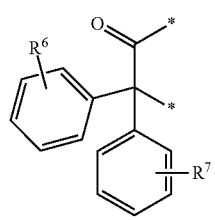

a

-continued

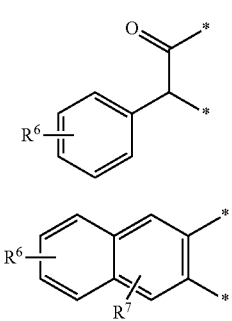

in which $R^6$ and $R^7$ are hydrogen, o=1 and p=0, and $R^1$ is phenyl, o=1 and p=1, and $R^1$ and $R^2$ together form a one residue selected from the group consisting of a, b and c, $R^3$, $R^4$ and $R^5$ are the same or different and are hydrogen, $C_{1-8}$-alkyl or allyl, or $R^3$ and $R^4$ together with the nitrogen to which they are attached form a morpholino ring.

Examples of $C_{1-8}$-alkyl are methyl, ethyl, propyl, isopropyl, butyl, sec-butyl, isobutyl and tert-butyl, pentyl, hexyl, heptyl, octyl and 2-ethylhexyl.

In especially preferred compositions of the present invention, in which X is silicon, the amine salt of the organic metal compound of formula I is selected from the group consisting of

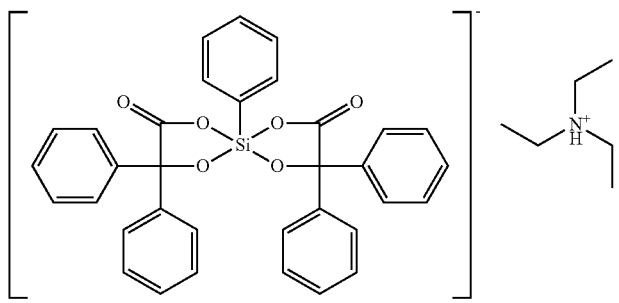

(I1)

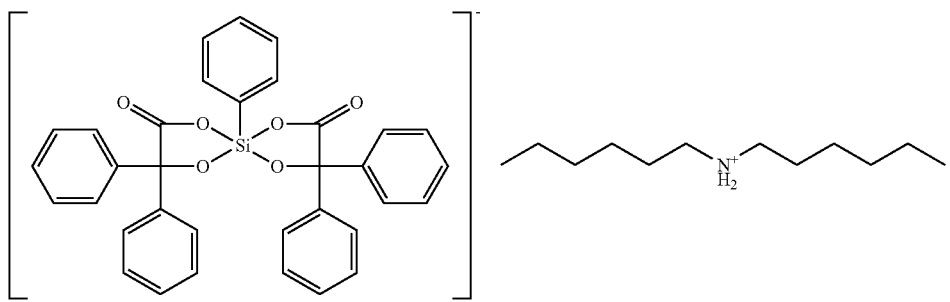

(I2)

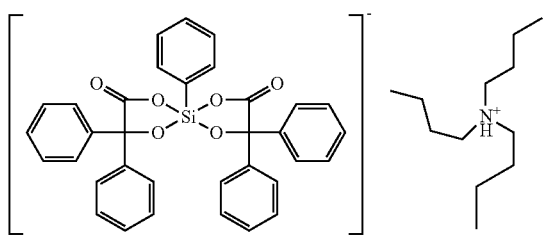

(I3)

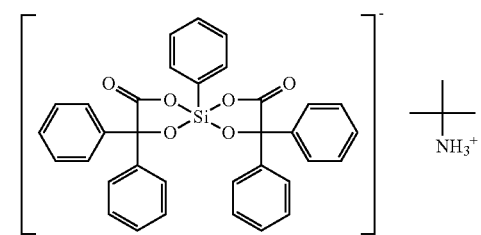

(I4)

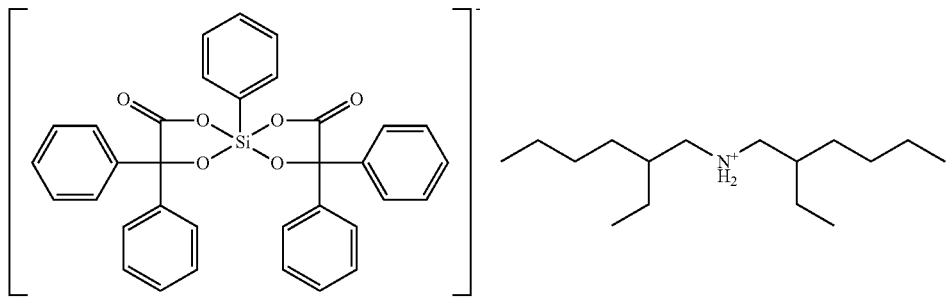

(I5)

-continued
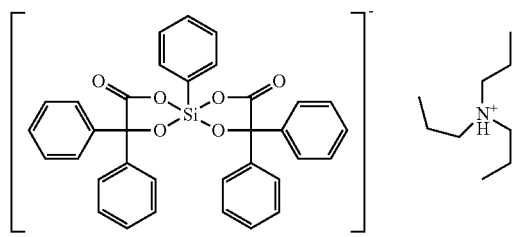 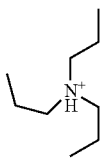
(I6)
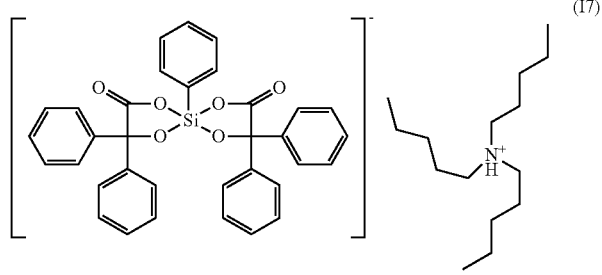 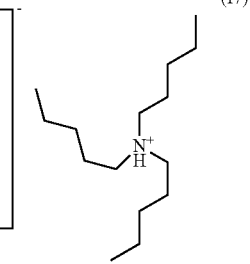
(I7)
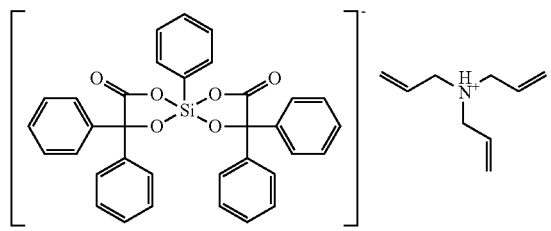
(I8)
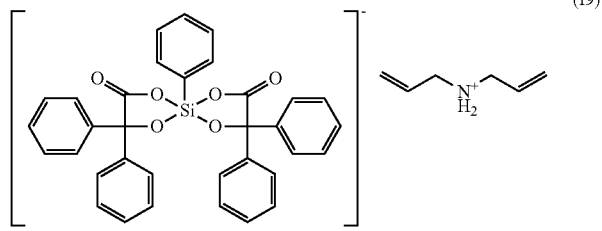
(I9)
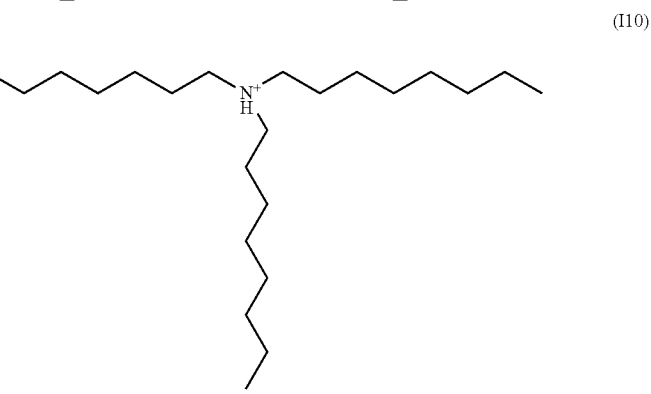
(I10)
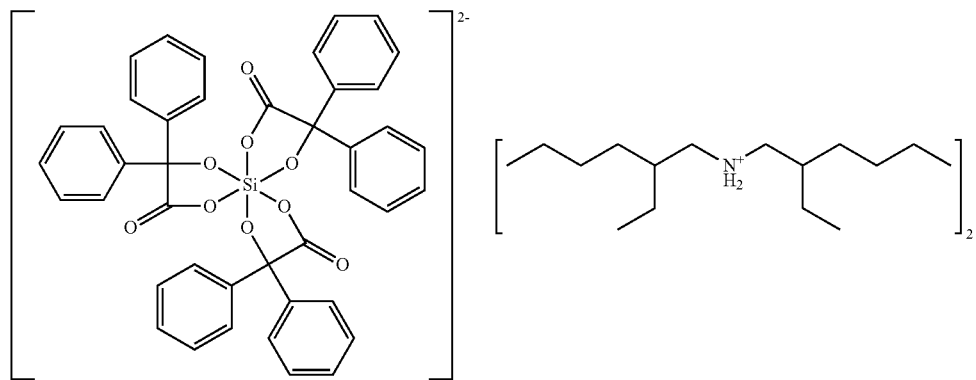
(I11)
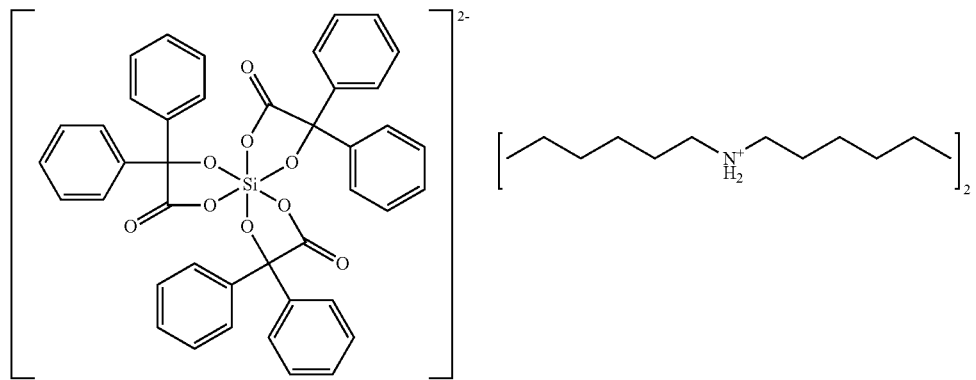
(I12)

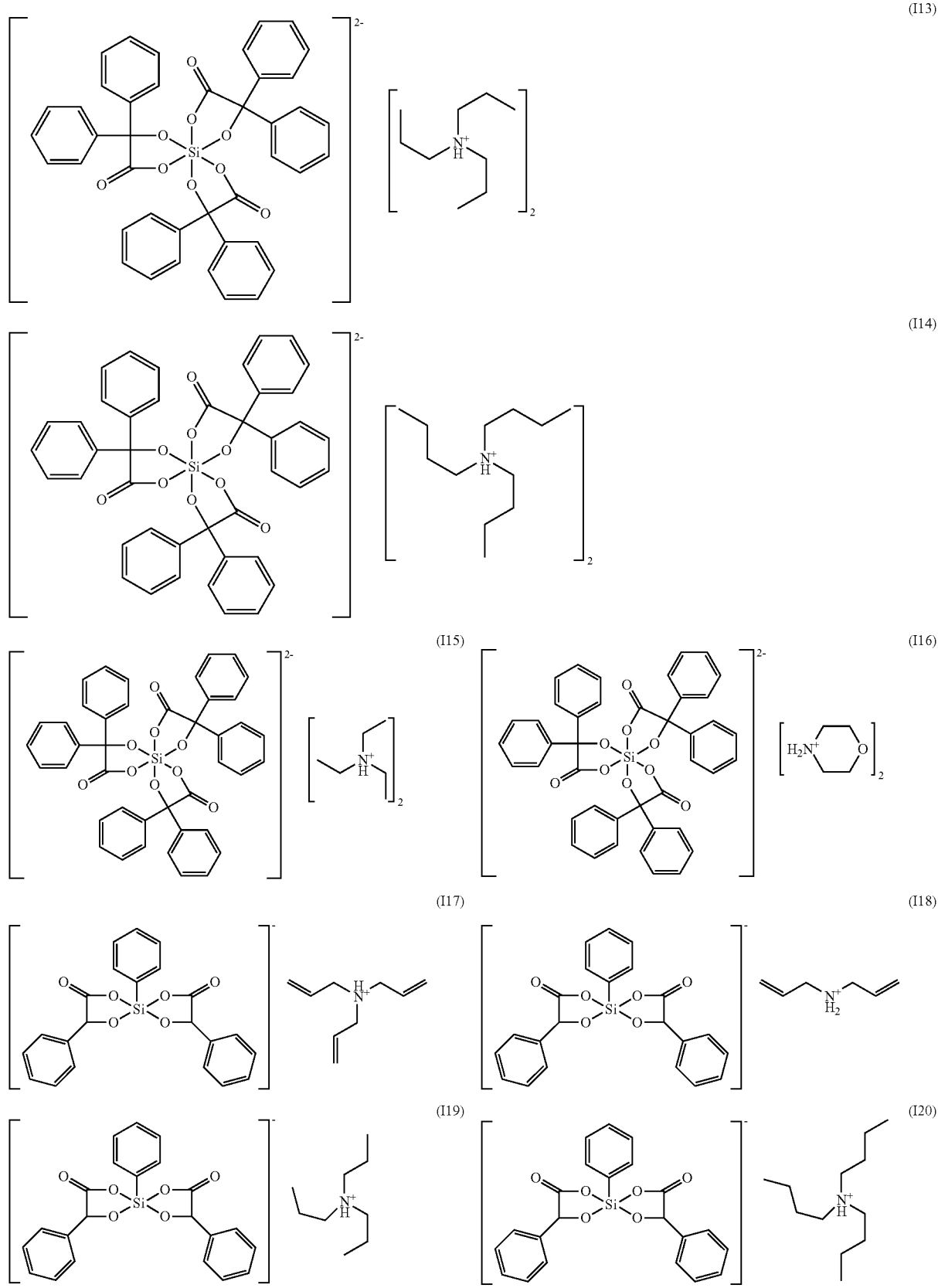

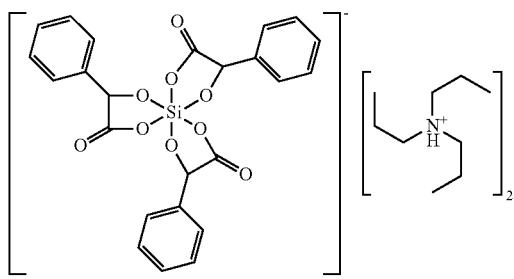
(I21)
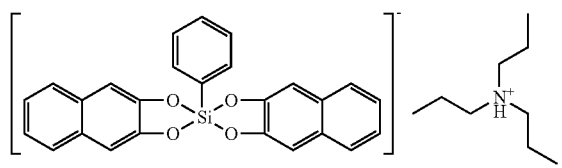
(I22)
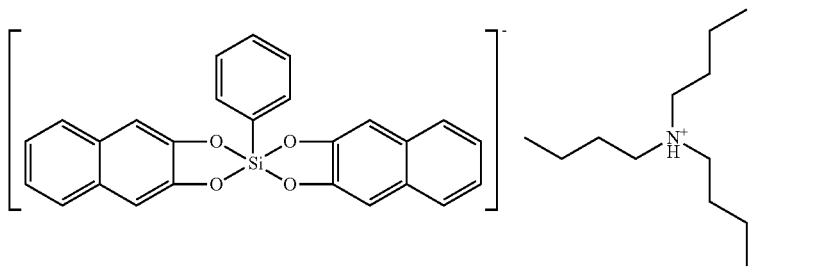
(I23)
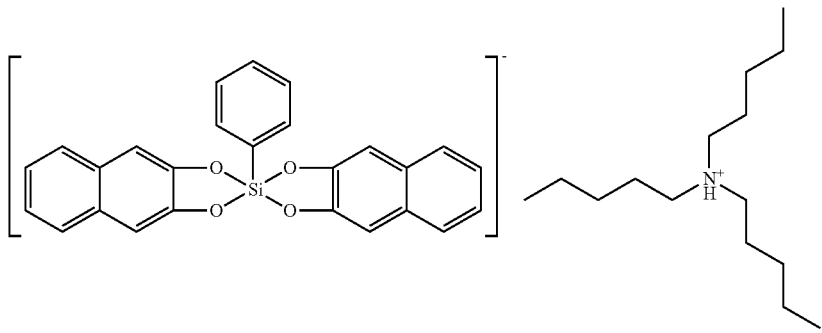
(I24)
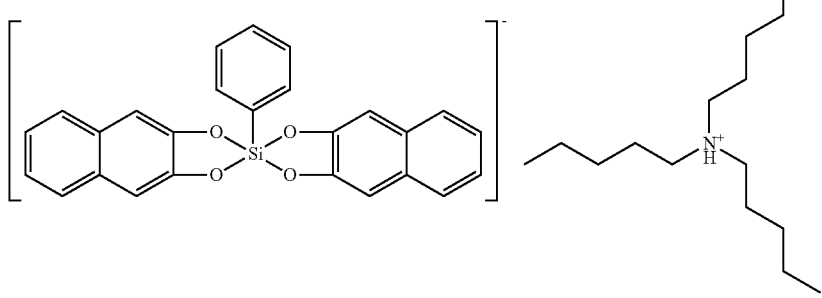
(I25)
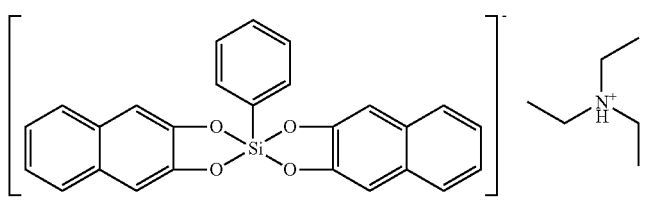
(I26)
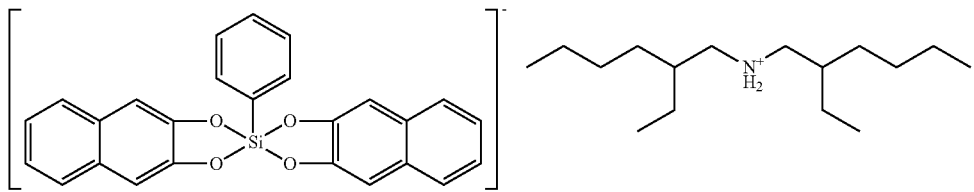
(I27)

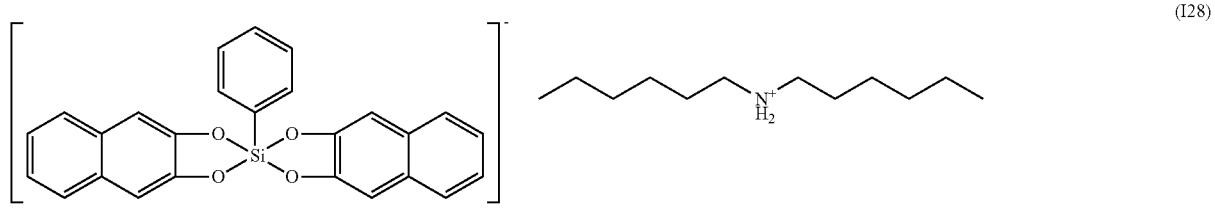

In preferred compositions of the present invention, in which X is boron,

E and F are the same or different and are selected from the group consisting of

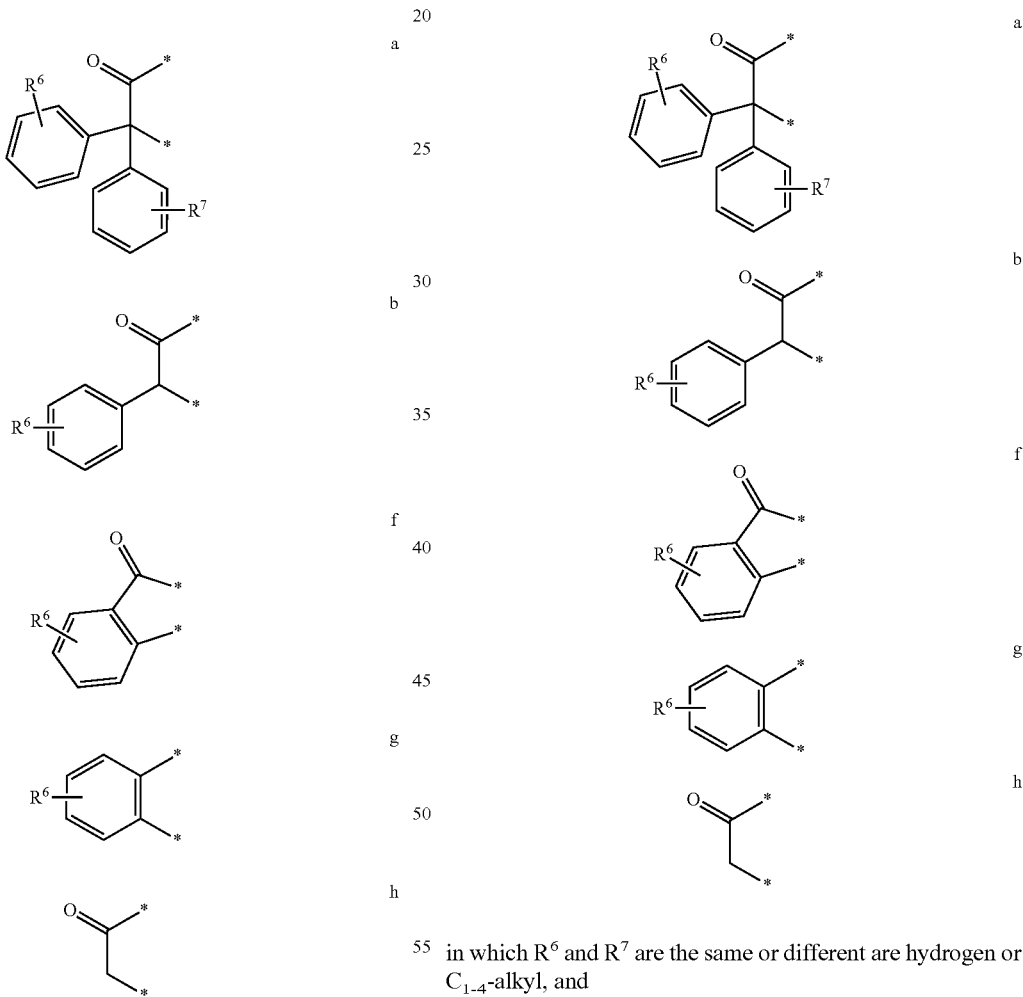

in which $R^6$ and $R^7$ are the same or different are hydrogen, $C_{1-4}$-alkyl, $C_{1-4}$-alkoxy, halogen, amino or carboxy, and o=0 and p=0, and $R^3$, $R^4$ and $R^5$ are the same or different and are hydrogen, $C_{1-12}$-alkyl, $C_{1-6}$-hydroxyalkyl, allyl, aralkyl or arylsulfonyl, in which aralkyl or arylsulfonyl can be substituted with $C_{1-4}$-alkyl, or $R^3$ and $R^4$ together with the nitrogen to which they are attached form a morpholino or piperidino ring.

In more preferred compositions of the present invention, in which X is boron,

E and F are the same or different and are selected from the group consisting of in which $R^6$ and $R^7$ are the same or different are hydrogen or $C_{1-4}$-alkyl, and o=0 and p=0, and $R^3$, $R^4$ and $R^5$ are the same or different and are hydrogen, $C_{1-10}$-alkyl, allyl or aralkyl, in which aralkyl can be substituted with $C_{1-4}$-alkyl, or $R^3$ and $R^4$ together with the nitrogen to which they are attached form a morpholino ring.

In most preferred compositions of the present invention, in which X is boron,

E and F are the same and are selected from the group consisting of a
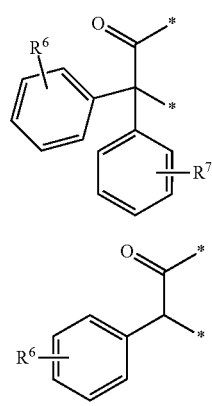
f
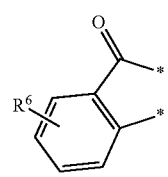
in which $R^6$ and $R^7$ are hydrogen, and
o=0 and p=0, and
$R^3$, $R^4$ and $R^5$ are the same or different and are hydrogen, $C_{1-8}$-alkyl or allyl.
In especially preferred compositions of the present invention, in which X is boron, the amine salt of the organic metal compound of formula I is selected from the group consisting of
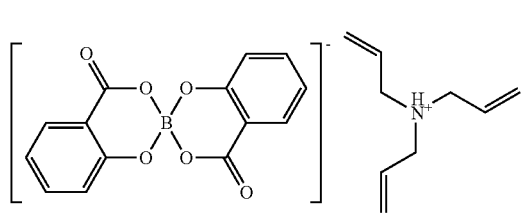
(I29)
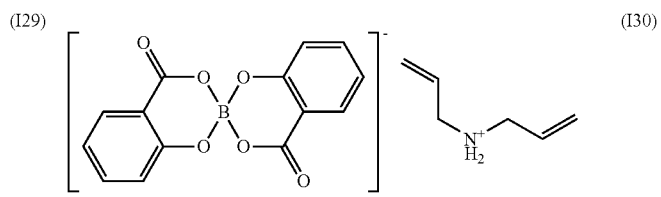
(I30)
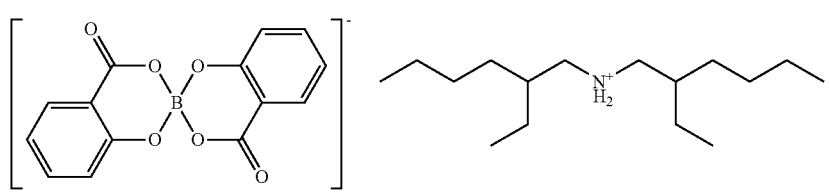
(I31)
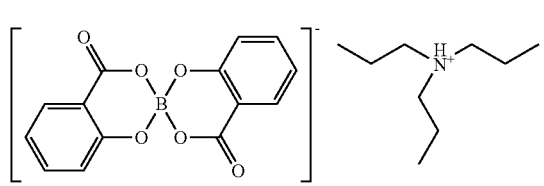
(I32)
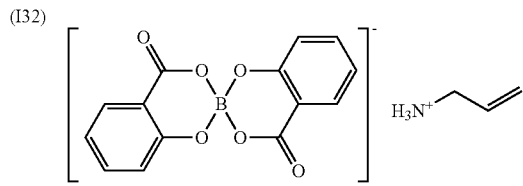
(I33)
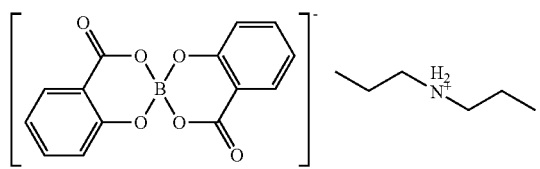
(I34)
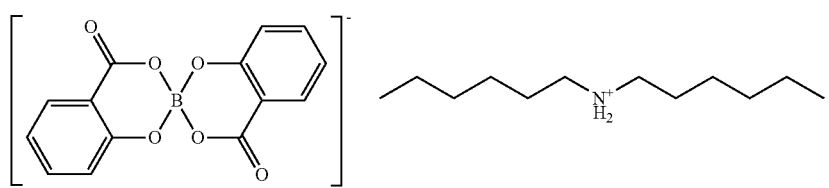
(I35)

-continued
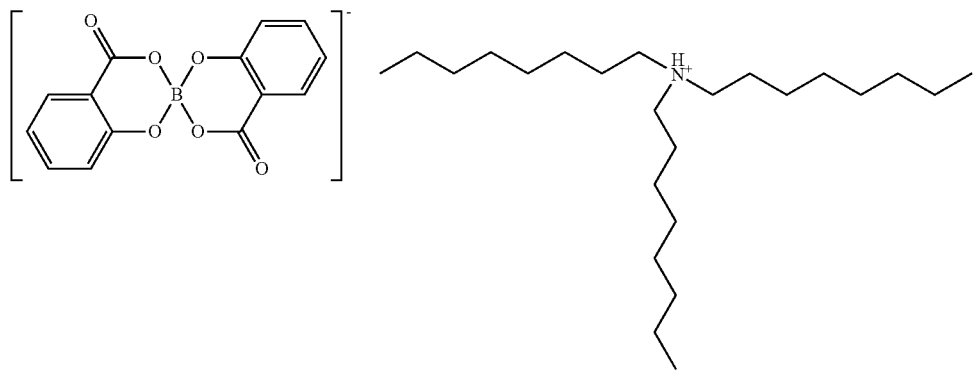
(I36)
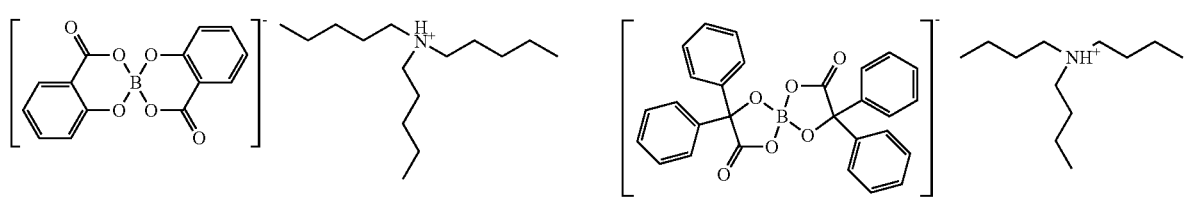
(I37) (I38)
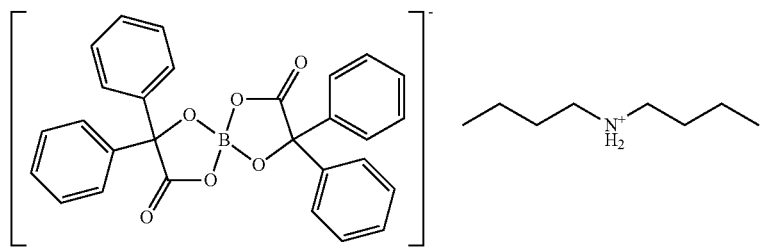
(I39)
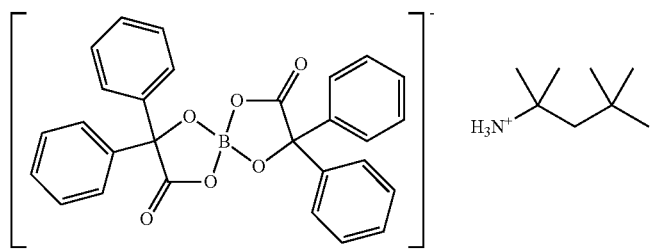
(I40)
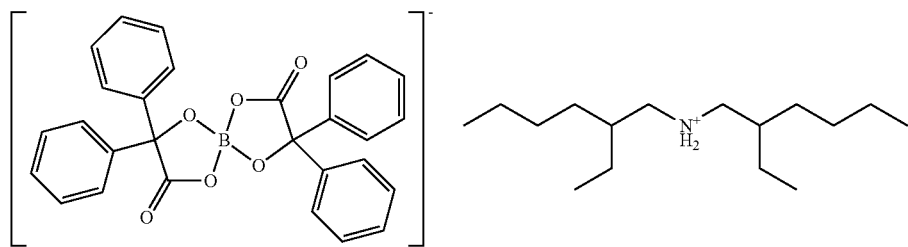
(I41)
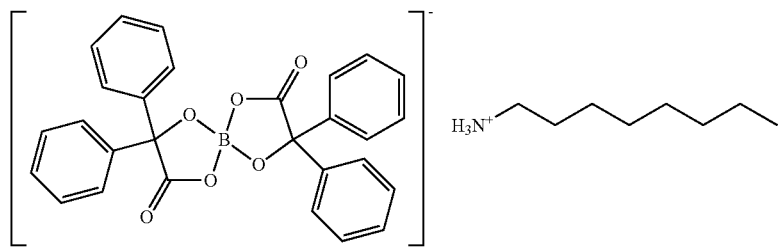
(I42)

-continued
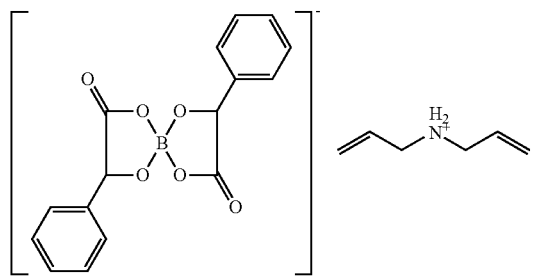 (I43)
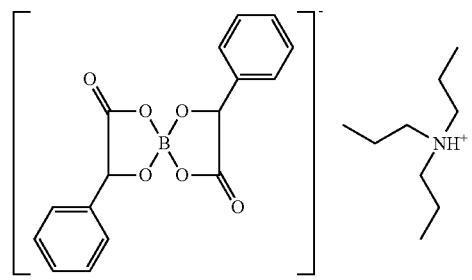 (I44)
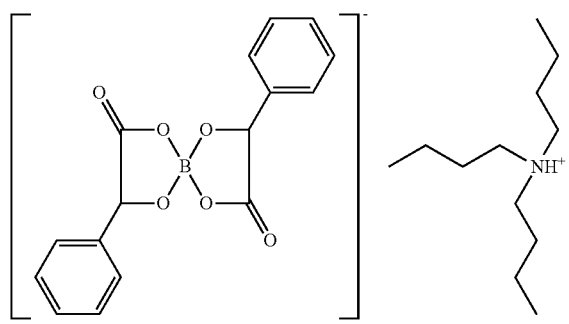 (I45)
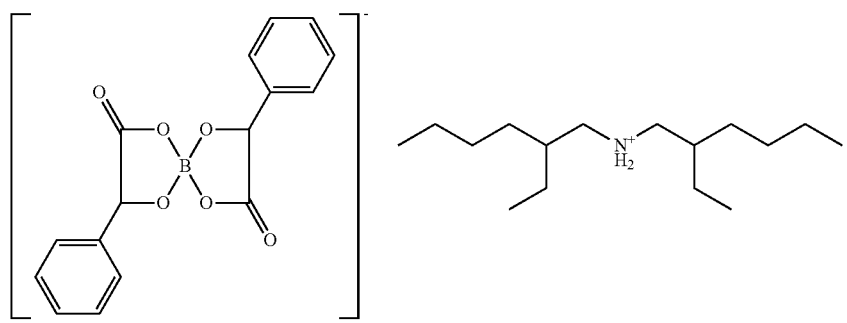 (I46)
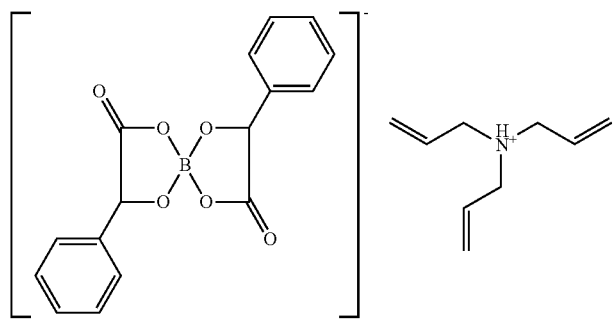 (I47)
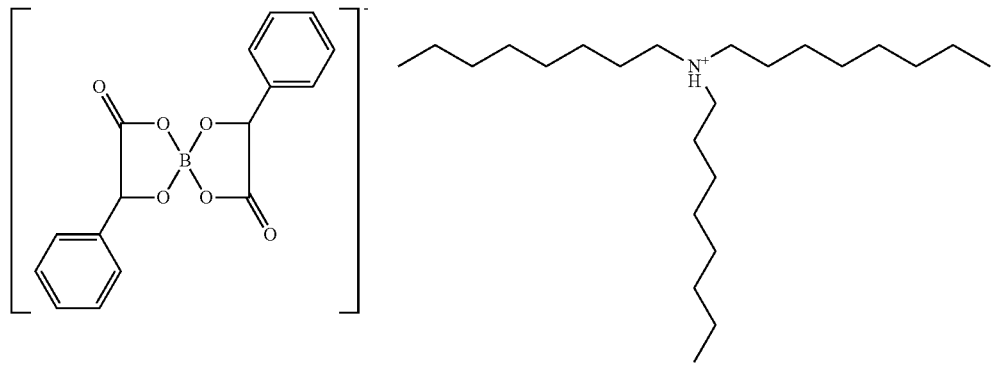 (I48)

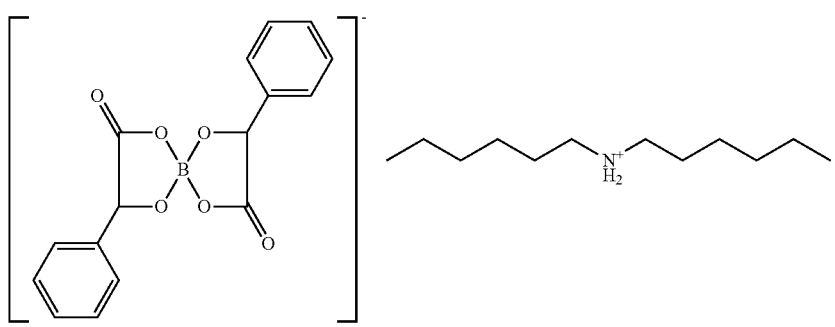

(I49)

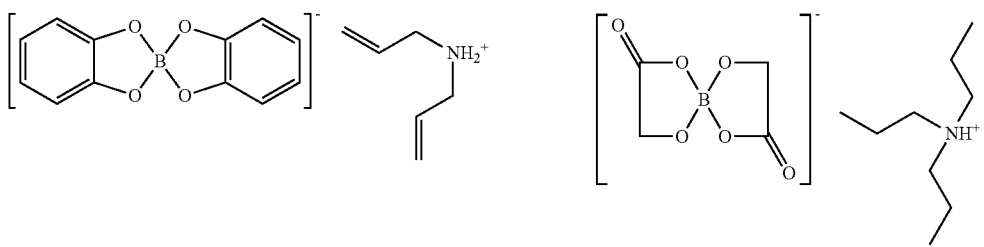

(I50)

(I52)

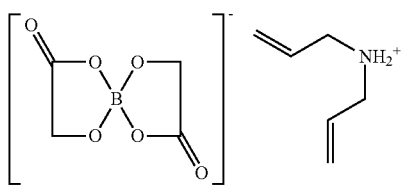

The amine salt of the organic metal compound of formula I can be prepared by reacting a silane such as phenyl triethoxysilane, a silicate such as tetraethylorthosilicate, or boric acid with the respective compound of the formula OH-E-OH and/or OH—F—OH in the presence of the respective amine of the formula $NR^3R^4R^5$. If the starting material is a silane or boric acid, 2 mol equivalents OH-E-OH and/or OH—F—OH and 1 mol equivalent of $NR^3R^4R^5$ are used. If the starting material is a silicate, 3 mol equivalents OH-E-OH and/or OH—F—OH and 2 mol equivalents of $NR^3R^4R^5$ are used. The reaction can be performed in any suitable organic solvent. If the starting material is a silane or a silicate, the reaction is preferably performed in tetrahydrofurane. If the starting material is boric acid, the reaction is preferably performed in a mixture of methanol and water.

The compositions of the present invention consist of the colour former in an amount of from 0.01 to 50%, the amine salt of the organic metal compound of formula I in an amount of from 0.01 to 50%, a binder in an amount of from 1 to 80%, a solvent in an amount of from 1 to 99%, and optional additional components in an amount of from 0 to 20%, wherein each amount is by weight based on the weight of the composition.

Preferably, the composition consist of the colour former in an amount of from 0.1 to 30%, the amine salt of the organic metal compound of formula I in an amount of from 0.1 to 30%, the binder in an amount of from 1 to 60% and the solvent in an amount of from 20 to 99%, and optional additional components in an amount of from 0 to 10%, wherein each amount is by weight based on the weight of the composition.

More preferably, the composition consist of the colour former in an amount of from 0.1 to 10%, the amine salt of the organic metal compound of formula I in an amount of from 0.1 to 10%, the binder in an amount of from 1 to 30% and the solvent in an amount of from 50 to 99%, and optional additional components in an amount of from 0 to 5%, wherein each amount is by weight based on the weight of the composition.

Most preferably, the composition consist of the colour former in an amount of from 1 to 5%, the amine salt of the organic metal compound of formula I in an amount of from 1 to 5%, the binder in an amount of from 5 to 15% and the solvent in an amount of from 70 to 90%, and optional additional components in an amount of from 0 to 3%, wherein each amount is by weight based on the weight of the composition.

The colour former can be any suitable colour former. Suitable colour former can be selected from the group consisting of phthalides, fluorans, triarylmethanes, benzoxazines, quinazolines, spiropyrans, quinones, thiazines, oxazines and mixtures thereof.

Examples of phthalides are crystal violet lactone (3,3-bis(p-dimethylaminophenyl)-6-dimethyl-aminophtalide), 3,3-bis(p-dimethylaminophenyl)phthalide, 3,3-bis(1-ethyl-2-methylindol-3-yl)phthalide, 3,3-bis(1-octyl-2-methylindol-3-yl)phthalide (sold for example under the tradename Ciba® Pergascript® Red I 6 B), 3-(4-diethylaminophenyl)-3-(1-ethyl-2-methyl-indol-3-yl)-phthalide, 7-(N-ethyl-N-isopentylamino)-3-methyl-1-phenylspiro[4H-chromeno-[2,3-c]pyrazole-4(1H)-3'phthalide, 3,6,6'-tris(dimethylamino)spiro[fluorene-9,3'-phthalide], 3,6,6'-tris(diethylamino)spiro[fluorene-9,3'-phthalide], 3,3-bis-[2-(p-dimethylaminophenyl)-2-(p-methoxyphenyl)ethenyl-4,5,6,7-tetrabromophthalide, 3,3-bis-[2-(p-dimethylaminophenyl)-2-(p-methoxyphenyl)ethenyl-4,5,6,7-tetrachlorophthalide, 3,3-bis[1,1-bis(4-pyrro-lidinophenyl)

ethylene-2-yl]-4,5,6,7-tetrabromophthalide, 3,3-bis-[1-(4-methoxyphenyl)-1-(4-pyrridinophenyl)ethylene-2-yl]-4,5,6,7-tetrachlorophthalide, 3-(4-diethylamino-2-ethoxyphenyl)-3-(1-ethyl-2-methylindol-3-yl)-4-azaphthalide, 3-(4-diethylamino-2-ethoxyphenyl)-3-(1-octyl-2-methylindol-3-yl)-4-azaphthalide and 3-(4-cyclohexylethylamino-2-methoxy-phenyl)-3-(1-ethyl-2-methylindol-3-yl)-4-azaphthalide The phthalides can be prepared by methods known in the art, for example crystal violet lactone can be prepared as described in GB 1,347,467, and 3,3-bis(1-ethyl-2-methylindol-3-yl)phthalide can be prepared as described in GB 1,389,716.

Examples of fluorans are are 3-di(ethyl)amino-6-methyl-7-(tert-butoxycarbonyl)anilinofluoran, 3-diethylamino-7-dibenzylaminofluoran, 3-dibutylamino-7-dibenzylaminofluoran, 3-diethyl-amino-6-methyl-7-(dibenzylamino) fluoran, 3-diethylamino-6-methylfluoran, 3-diethylamino-6-chloro-7-methylfluoran, 3-diethylamino-6-methyl-7-chlorofluoran, 3-diethylamino-7-tert-butylfluoran, 3-diethylamino-7-(ethoxycarbonyl)-fluoran (as sold for example under the tradename Ciba® Pergascript® Orange IG), 3-diethylamino-7-methylfluoran, 3-diethylamino-6,8-dimethylfluoran, 3-diethylamino-7-chlorofluoran, 3-dibutylamino-6-methylfluoran, 3-cyclohexylamino-6-chlorofluoran, 3-diethylamino-benzo[a]fluoran, 3-diethylamino-benzo[c]fluoran, 3-dimethylamino-6-methyl-7-anilinofluoran, 3-diethylamino-6-methyl-7-anilinofluoran, 3-diethylamino-6-methyl-7-(2,4-dimethylanilino)fluoran, 3-diethylamino-6-methyl-7-(3-trifluoromethylanilino)fluoran, 3-diethylamino-6-methyl-7-(2-chloroanilino)-fluoran, 3-diethylamino-6-methyl-7-(p-chloroanilino)fluoran, 3-diethylamino-6-methyl-7-(2-fluoroanilino)fluoran, 3-diethylamino-6-methyl-7-(p-octylanilino)fluoran, 3-diethylamino-7-(p-octylanilino)fluoran, 3-diethylamino-6-methyl-7-(p-methylanilino)fluoran, 3-diethylamino-6-ethoxyethyl-7-anilinofluoran, 3-diethylamino-6-methyl-7-(3-methylanilino)fluoran, 3-diethyl-amino-7-(3-trifluoromethylanilino)fluoran, 3-diethylamino-7-(2-chloroanilino)fluoran, 3-diethyl-amino-7-(2-fluoroanilino) fluoran, 3-diethylamino-6-chloro-7-anilinofluoran, 3-dibutylamino-6-methyl-7-anilinofluoran (as sold for example under the tradename Ciba® Pergascript® Black I-2R), 3-dibutylamino-6-methyl-7-(2,4-dimethylanilino) fluoran, 3-dibutylamino-6-methyl-7-(2-chloroanilino)fluoran, 3-dibutylamino-6-methyl-7-(4-chloroanilino)fluoran, 3-dibutylamino-6-methyl-7-(2-fluoroanilino)fluoran, 3-dibutylamino-6-methyl-7-(3-trifluoromethyl-anilino)fluoran, 3-dibutylamino-6-ethoxyethyl-7-anilinofluoran, 3-dibutylamino-6-chloro-anilinofluoran, 3-dibutylamino-6-methyl-7-(4-methylanilino)fluoran, 3-dibutylamino-7-(2-chloroanilino)fluoran, 3-dibutylamino-7-(2-fluoroanilino) fluoran, 3-dipentylamino-6-methyl-7-anilinofluoran, 3-dipentylamino-6-methyl-7-(4-2-chloroanilino)fluoran, 3-dipentyl-amino-7-(3-trifluoromethylanilino)fluoran, 3-dipentylamino-6-chloro-7-anilinofluoran, 3-dipentylamino-7-(4-chloroanilino)fluoran, 3-pyrrolidino-6-methyl-7-anilinofluoran, 3-piperidino-6-methyl-7-anilinofluoran, 3-(N-methyl-N-propylamino)-6-methyl-7-anilinofluoran, 3-(N-methyl-N-cyclohexylamino)-6-methyl-7-anilinofluoran, 3-(N-ethyl-N-cyclohexylamino)-6-methyl-7-anilinofluoran, 3-(N-ethyl-N-hexylamino)-7-anilinofluoran, 3-(N-ethyl-p-toluidino)-amino-6-methyl-7-anilinofluoran, 3-(N-ethyl-p-toluidino)amino-7-methylfluoran, 3-(N-ethyl-N-isoamylamino)-6-methyl-7-anilinofluoran, 3-(N-ethyl-N-isoamylamino)-7-(2-chloroanilino)-fluoran, 3-(N-ethyl-N-isoamylamino)-6-chloro-7-anilinofluoran, 3-(N-ethyl-N-tetrahydrofurfuryl-amino)-6-methyl-7-anilinofluoran, 3-(N-ethyl-N-isobutylamino)-6-methyl-7-anilinofluoran, 3-(N-butyl-N-isoamylamino)-6-methyl-7-anilinofluoran, 3-(N-isopropyl-N-3-pentylamino)-6-methyl-7-anilinofluoran, 3-(N-ethyl-N-ethoxypropylamino)-6-methyl-7-anilinofluoran, 2-methyl-6-p-(p-dimethylaminophenyl)aminoanilinofluoran, 2-methoxy-6-p-(p-dimethyl-aminophenyl)aminoanilinofluoran, 2-chloro-3-methyl-6-p-(p-phenylaminophenyl)amino-anilinofluoran, 2-diethylamino-6-p-(p-dimethylaminophenyl)aminoanilinofluoran, 2-phenyl-6-methyl-6-p-(p-phenylaminophenyl)aminoanilinofluoran, 2-benzyl-6-p-(p-phenylamino-phenyl)aminoanilinofluoran, 3-methyl-6-p-(p-dimethylaminophenyl)aminoanilinofluoran, 3-diethylamino-6-p-(p-diethylaminophenyl)aminoanilinofluoran, 3-diethylamino-6-p-(p-dibutyl-aminophenyl)aminoanilinofluoran and 2,4-dimethyl-6-[(4-dimethylamino)anilino]fluoran.

The fluorans can be prepared by methods known in the art, for example 3-diethylamino-7-di-benzylaminofluoran, 3-diethylamino-7-tert-butylfluoran, 3-diethylamino-6-methyl-7-anilino-fluoran and 3-diethylamino-6-methyl-7-(2,4-dimethylanilino)fluoran and can be prepared as described in U.S. Pat. No. 5,166,350 A, 3-diethylamino-6-methyl-7-(3-methylanilino)fluoran can be prepared as described in EP 0 546 577 A1,3-diethylamino-6-chloro-7-anilinofluoran can be prepared as described in DE 2130845, 3-pyrrolidino-6-methyl-7-anilinofluoran and 3-piperidino-6-methyl-7-anilinofluoran can be prepared as described in U.S. Pat. No. 3,959,571 A, 3-(N-ethyl-N-isoamylamino)-6-methyl-7-anilinofluoran can be prepared as described in GB 2 002 801 A, and 3-(N-methyl-N-propylamino)-6-methyl-7-anilinofluoran can be prepared as described in GB 2 154 597 A.

Examples of benzoxazines are 2-phenyl-4-(4-diethylaminophenyl)-4-(4-methoxyphenyl)-6-methyl-7-dimethylamino-3,1-benzoxazine, which can be prepared as described in EP 0 187 329 A1, and 2-phenyl-4-(4-diethylaminophenyl)-4-(4-methoxyphenyl)-8-methyl-7-dimethylamino-3,1-benzoxazine.

An example of a quinazoline is 4,4'-[1-methylethylidene) bis(4,1-phenyleneoxy-4,2-quina-zolinediyl)]bis[N,N-diethylbenzeneamine]. An example of a triarylmethane is bis(N-methyldi-phenylamine)-4-yl-(N-butylcarbazole)-3-yl-methane, which can be prepared as described in GB 1,548,059.

Examples of spiropyrans are 1',3',3'-trimethylspiro[2H-1-benzopyran-2,2'-indoline], 1,3,3-tri-methylspiro[indoline-2,3'-[3H]naphth[2,1-b][1,4]oxazine] and 1',3',3'-trimethyl-spiro-[2H-1-benzothiopyran-2,2'-indoline].

An example of a quinone is hematoxyline. An example of an oxazine is 3,7-bis(dimethyl-amino)-10-benzoylphenoxazine. An example of a thiazine is 3,7-bis(dimethylamino)-10-benzoylphenothiazine.

Preferably, the colour former is a phthalide or a fluoran or mixtures thereof.

More preferably, the colour former is crystal violet lactone, 3,3-bis(1-octyl-2-methylindol-3-yl)phthalide (sold for example under the tradename Ciba® Pergascript® Red I6 B), 3-di-ethylamino-7-(ethoxycarbonyl)-fluoran (as sold for example under the trade name Ciba® Pergascript® Orange IG) or 3-dibutylamino-6-methyl-7-anilinofluoran (as sold for example under the trade name Ciba® Pergascript® Black I-2R).

The binder can be any suitable binder. Preferably, the binder is a polymeric binder. Examples of polymeric binders are acrylic polymers, styrene polymers and hydrogenated products thereof, vinyl polymers, polyolefins and hydrogenated or epoxidized products thereof, aldehyde polymers, epoxide polymers, polyamides, polyesters, polyurethanes, sulfone-based polymers and natural polymers and derivatives thereof. The polymeric binder can also be a mixture of polymeric binders.

Acrylic polymers are polymers formed from at least one acrylic monomer or from at least one acrylic monomer and at least one styrene monomer, vinyl monomer, olefin monomer and/or maleic monomer.

Examples of acrylic monomers are acrylic acid or salts thereof, acrylamide, acrylonitrile, $C_{1-6}$-alkyl acrylates such as ethyl acrylate, butyl acrylate or hexyl acrylate, di($C_{1-4}$-alkyl-amino)$C_{1-6}$-alkyl acrylates such as dimethylaminoethyl acrylate or diethylaminoethyl acrylate and $C_{1-4}$-alkyl halide adducts thereof such as dimethylaminoethyl acrylate methyl chloride, amides formed from di($C_{1-4}$-alkylamino) $C_{1-6}$-alkylamines and acrylic acid and $C_{1-4}$-alkyl halide adducts thereof, methacrylic acid or salts thereof, methacrylamide, methacrylonitrile, $C_{1-6}$-alkyl methacrylates such as methyl methacrylate or ethyl methacrylate, di($C_{1-4}$-alkyl-amino)$C_{1-6}$-alkyl methacrylates and $C_{1-4}$-alkyl halide adducts thereof, amides formed from di($C_{1-4}$-alkylamino) $C_{1-6}$-alkylamines and methacrylic acid and $C_{1-4}$-alkyl halide adducts thereof and crosslinker such as N,N'-methylenebisacrylamide.

Examples of styrene monomers are styrene, 4-methylstyrene and 4-vinylbiphenyl. Examples of vinyl monomers are vinyl alcohol, vinyl chloride, vinylidene chloride, vinyl isobutyl ether and vinyl acetate. Examples of olefin monomers are ethylene, propylene, butadiene and isoprene and chlorinated or fluorinated derivatives thereof such as tetrafluoroethylene. Examples of maleic monomers are maleic acid, maleic anhydride and maleimide.

Examples of acrylic polymers are poly(methyl methacrylate), poly(butyl methacrylate) and styrene acrylic polymers.

Styrene polymers are polymers formed from at least one styrene monomer and at least one vinyl monomer, olefin monomer and/or maleic monomer. Examples of styrene monomers, vinyl monomers, olefin monomers and maleic monomers are given above. Examples of styrene polymers are styrene butadiene styrene block polymers, styrene ethylene butadiene block polymers, styrene ethylene propylene styrene block polymers.

Vinyl polymers are polymers formed from at least one vinyl monomer or from at least one vinyl monomer and at least one olefin monomer or maleic monomer. Examples of vinyl monomers, olefin monomers and maleic monomers are given above. Examples of vinyl polymers are polyvinyl chloride and polyvinylalcohol.

Polypolefins are polymers formed from at least one olefin monomer. Examples of olefin monomers are given above. Examples of polyolefines are polyethylene, polypropylene and polybutadiene.

Aldehyde polymers are polymers formed from at least one aldehyde monomer or polymer and at least one alcohol monomer or polymer, amine monomer or polymer and/or urea monomer or polymer. Examples of aldehyde monomers are formaldehyde, furfural and butyral. Examples of alcohol monomers are phenol, cresol, resorcinol and xylenol. An example of polyalcohol is polyvinyl alcohol. Examples of amine monomers are aniline and melamine. Examples of urea monomers are urea, thiurea and dicyandiamide. An example of an aldehyde polymer is polyvinyl butyral formed from butyral and polyvinylalcohol.

Epoxide polymers are polymers formed from at least one epoxide monomer and at least one alcohol monomer and/or amine monomer. Examples of epoxide monomers are epichlorhydrine and glycidol. Examples of alcohol monomers are phenol, cresol, resorcinol, xylenol, bisphenol A and glycol. An example of epoxide polymer is phenoxy resin, which is formed from epichlorihydrin and bisphenol A.

Polyamides are polymers formed from at least one monomer having an amide group or an amino as well as a carboxy group or from at least one monomer having two amino groups and at least one monomer having two carboxy groups. An example of a monomer having an amide group is caprolactam. An example of a diamine is 1,6-diaminohexane. Examples of dicarboxylic acids are adipic acid, terephthalic acid, isophthalic acid and 1,4-naphthalene-dicarboxylic acid. Examples of polyamides are poyhexamethylene adipamide and polycaprolactam.

Polyesters polymers formed from at least one monomer having an hydroxy as well as a carboxy group or from at least one monomer having two hydroxy groups and at least one monomer having two carboxy groups or a lactone group. An example of a monomer having a hydroxy as well as a carboxy group is adipic acid. An example of a diol is ethylene glycol. An example of a monomer having a lactone group is carprolactone. Examples of dicarboxylic acids are terephthalic acid, isophthalic acid and 1,4-naphthalenedicarboxylic acid. An examples of polyesters is polyethylene terephthalate. So-called alkyd resins are also regarded to belong to polyester polymers.

Polyurethane are polymers formed from at least one diisocyanate monomer and at least one polyol monomer and/or polyamine monomer. Examples of diisocyanate monomers are hexamethylene diisocyanate, toluene diisiocyanate and diphenylmethane diiscocyanate.

Examples of sulfone-based polymers are polyarylsulfone, polyethersulfone, polyphenyl-sulfone and polysulfone. Polysulfone is a polymer formed from 4,4-dichlorodiphenyl sulfone and bisphenol A.

Natural polymers can be a cellulose, natural rubber or gelatin. Examples of cellulose derivatives are ethyl cellulose, hydroxypropyl cellulose, nitrocellulose, cellulose acetate and cellulose propionate.

The polymeric binders are known in the art and can be produced by known methods. The polymeric binder can be also produced in situ by UV radiation of a composition comprising monomers, capable of radical polymerisation, and a UV sensitive initiator.

Preferred polymeric binders are acrylic polymers, vinyl polymers, aldehyde polymers, epoxide polymers, polyamides, polyesters and natural polymers and derivatives thereof. More preferred polymeric binders acrylic polymers, vinyl polymers, natural polymers and derivatives thereof.

Even more preferred polymeric binders are poly(methyl methacrylate), poly(butyl meth-acrylate), polyvinyl alcohol and cellulose.

The most preferred polymeric binder is poly(methyl methacrylate).

The solvent can be any suitable solvent. A suitable solvent can be selected from the group consisting of organic solvents, mixtures of organic solvents, and mixtures of one or more organic solvent with water. Preferably, the solvent is an organic solvent or a mixture of organic solvents. More preferably, the solvent is an organic solvent or a mixture of organic solvents wherein the organic solvent or solvents are selected from the group consisting of $C_{1-4}$-alkanols, $C_{1-4}$-polyols, $C_{1-4}$-alkyl $C_{1-4}$-alkanoates, $C_{3-6}$-ketones, $C_{4-6}$-ethers, $C_{2-3}$-nitriles, nitromethane, dimethylsulfoxide, dimethylformamide, dimethylacetamide, N-methyl pyrolidone and sulfolane, whereby $C_{1-4}$-alkanols, $C_{1-4}$-polyols and $C_{1-4}$-alkyl $C_{1-4}$-alkanoates may be substituted with $C_{1-4}$-alkoxy.

Examples of $C_{1-4}$-alkanols are methanol, ethanol, propanol, isopropanol or butanol, iso-butanol, sec-butanol and tert-butanol. Examples of a $C_{1-4}$-alkoxyderivatives thereof are 2-ethoxyethanol and 1-methoxy-2-propanol. Examples of $C_{1-4}$-polyols are glycol and glycerol. Examples of $C_{1-4}$-alkyl $C_{1-4}$-alkanoates are ethyl acetate, butyl acetate, ethyl propionate and ethyl butanoate. Examples of $C_{1-4}$-alkoxy derivatives thereof are 2-ethoxyethyl acetate and 2-methoxyethyl acetate. Examples of $C_{3-6}$-ketones are acetone and methyl ethyl ketone. Examples of $C_{4-6}$-ethers are dimethoxyethane, diisopropylethyl and tetrahydrofurane. An example of a $C_{2-3}$-nitrile is acetonitrile.

Most preferably, the solvent is an organic solvent or a mixture of organic solvents selected from the group consisting of $C_{1-4}$-alkanols, $C_{1-4}$-alkyl $C_{1-4}$-alkanoates and $C_{3-6}$-ketones. Most preferably, the organic solvent is a $C_{3-6}$-ketone or a mixture of $C_{3-6}$-ketones.

The optional additional components of composition of the present invention can be any other compound suitable for improving the performance of the composition. Examples of optional additional components are IR absorbers, UV absorbers, starting amine $NR^3R^4R^5$, stabilizers and antioxidants. The addition of an IR absorber increases, for example, the density of the image, whereas the addition of the starting amine $NR^3R^4R^5$ increases the background whiteness.

An example of an IR absorber are alkylated triphenyl phosphorothionates, for example as sold under the trade name Ciba® Irgalube® 211. An example of a UV absorber is 2-hydroxy-4-methoxybenzophenone.

The coating composition of the present invention can be a solution or dispersion such as an emulsion or suspension. Preferably, the coating composition is a solution, as these coating compositions yield transparent coatings.

Examples of coating compositions which are a solutions are compositions consisting of 1 to 5% of a colour former selected from the group consisting of crystal violet lactone, 3,3-bis-(1-octyl-2-methylindol-3-yl)phthalide (sold for example under the trade name Ciba® Pergascript® Red I6 B), 3-diethylamino-7-(ethoxycarbonyl)-fluoran (as sold for example under the tradename Ciba® Pergascript® Orange IG) and 3-dibutylamino-6-methyl-7-anilinofluoran (as sold for example under the tradename Ciba® Pergascript® Black I-2R), 1 to 5% of the amine salt of the organic metal compound of formula I1 to I52, 5 to 15% poly(methyl methacrylate) as binder, 70 to 90% of a solvent consisting of acetone and methyl ethyl ketone, and optional additional components in an amount of from 0 to 3%, wherein each amount is by weight based on the weight of the composition.

Preferred coating compositions which are a solutions are compositions consisting of 2.5 to 3.5% of a colour former selected from the group consisting of crystal violet lactone, 3,3-bis-(1-octyl-2-methylindol-3-yl)phthalide (sold for example under the tradename Ciba® Pergascript® Red I6 B), 3-diethylamino-7-(ethoxycarbonyl)-fluoran (as sold for example under the tradename Ciba® Pergascript® Orange IG) and 3-dibutylamino-6-methyl-7-anilinofluoran (as sold for example under the tradename Ciba® Pergascript® Black I-2R), 2.5 to 3.5% of the amine salt of the organic metal compound of formula I1 to I52, 8 to 12% poly(methyl methacrylate) as binder, 75 to 85% of a solvent consisting of acetone and methyl ethyl ketone in a ratio 1:1 to 1:4, and optional additional components in an amount of from 0 to 3%, wherein each amount is by weight based on the weight of the composition.

Also part of the invention is a process for preparing the composition of the present invention comprising the step of mixing the amine salt of the organic metal compound I, the colour developer, the binder, optionally additional components and the solvent. Preferably, the process comprises the steps of
i) mixing the amine salt of the organic metal compound of formula I and solvent,
ii) adding the colour former, the binder and optional additional components, and
iii) optionally diluting the composition to the desired concentration with further solvent.

Also part of the invention is a substrate coated with the coating composition of the present invention.

The substrate can be a sheet or any other three dimensional object and it can be transparent or opaque. The substrate can be made from paper, cardboard, metal, wood, textiles, glass, ceramics and/or polymers. Examples of polymers are polyethylene terephthalate, low density-polyethylene, polypropylene, biaxially orientated polypropylene, polyether sulfone, polyvinyl chloride polyester and polystyrene. Preferably, the substrate is made from paper, cardboard or polymer. More preferably, the substrate is a flexible polymer film made from polyethylene terephthalate, low density-polyethylene, polypropylene, biaxially orientated polypropylene, polyether sulfone or polyvinyl chloride.

The thickness of the coating usually chosen is in the range of 0.1 to 1000 μm. Preferably, it is in the range of 1 to 500 μm. More preferably, it is in the range of 1 to 200 μm. Most preferably, it is in the range of 5 to 150 μm.

Another aspect of the present invention is a process for preparing a coated substrate, which comprises the step of i) coating a substrate with the composition of the present invention.

The substrate can be coated with the composition of the present invention by using a standard coating application as such as a bar coater application, rotation application, spray application, curtain application, dip application, air application, knife application, blade application or roll application.

The coating composition can be dried, for example at ambient or elevated temperature.

Also part of the invention is a process for preparing a marked substrate, which comprises the steps of i) coating a substrate with the composition of the present invention, and ii) exposing those parts of the coated substrate, where a marking is intended, to energy in order to generate a colour marking.

The energy can be heat or any other energy, which is transformed into heat when applied to the substrate coated with the composition of the present invention. Examples of such energy are UV, IR or microwave irradiation.

The energy can be applied to the coated substrate in any suitable way, for example heat can be applied by using a thermal printer, and UV and IR irradiation can be applied by using a UV or IR laser. Examples of IR lasers are $CO_2$ lasers, Nd:YAG lasers and IR semiconductor lasers.

Preferably, the energy is IR irradiation. More preferably, the energy is IR irradiation having a wavelength in the range of 800 to 32000 nm. Most preferably, the energy is IR irradiation generated by a $CO_2$ laser or a Nd:YAG laser.

Typically the exact power of the IR laser and the line speed is determined by the application and chosen to be sufficient to generate the image, for example, when the wavelength of the IR laser is 10600 nm and the diameter of the laser beam is 0.35 mm, the power is typically 0.5 to 4 W, diameter and the line speed is typically 300 to 10000 mm/s.

Yet another aspect of the invention is the marked substrate, which is obtained by above process.

Also part of the invention are amine salts of the organic metal compound of formula

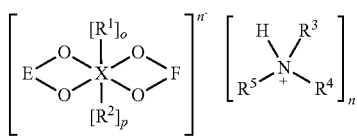

in which X is silicon or boron, and
E and F are the same or different and are selected from the group consisting of

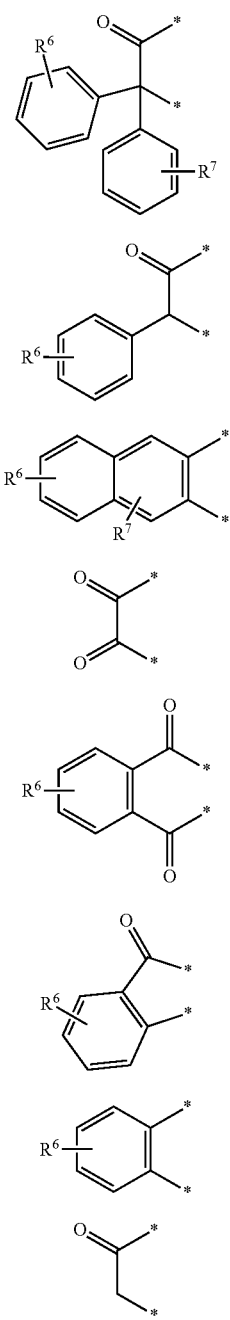

in which $R^6$ and $R^7$ are the same or different are hydrogen, $C_{1-4}$-alkyl, $C_{1-4}$-alkoxy, halogen, amino or carboxy, and for X=silicon o=1 and p=0, and $R^1$ is aryl, aralkyl or $C_{1-4}$-alkyl, or
o=1 and p=1, and $R^1$ and $R^2$ together form a one residue selected from the group consisting of a, b, c, d, e, f, g and h, and for X=boron o=0 and p=0, and $R^3$, $R^4$ and $R^5$ are the same or different and are hydrogen, $C_{1-12}$-alkyl, $C_{1-6}$-hydroxyalkyl, allyl, aralkyl or arylsulfonyl, in which aralkyl or arylsulfonyl can be substituted with $C_{1-4}$-alkyl, or $R^3$ and $R^4$ together with the nitrogen to which they are attached form a morpholino or piperidino ring, with the proviso that if X is silicon, E and F are both residue a, o=1 and p=1, and $R^1$ and $R^2$ together form residue a, then $R^3$, $R^4$ and $R^5$ are not all ethyl, if X is boron, E and F are both residue a, and o=0 and p=0, then $R^3$, $R^4$ and $R^5$ are not all butyl, if X is boron, E and F are both residue f, and o=0 and p=0, then $R^3$ and $R^4$ are not propyl and $R^5$ is not hydrogen or $R^3$ is not allyl and $R^4$ and $R^5$ are not hydrogen.

The coating compositions of the present invention have the advantage that they yield coloured images of excellent intensity and of high durability especially in terms of water resistance and abrasion resistance, and that they can be modulated in order to achieve either transparent or opaque coatings. In addition, the coating compositions do not yield colouration before the energy treatment and, if the coating composition of the present invention includes the starting amine $NR^3R^4R^5$ images with increased background whiteness can be obtained.

EXAMPLES

Example 1

Preparation of I7

Benzilic acid (9.495 g, 0.0416 mol) and phenyltriethoxysilane (5.0 g, 0.0208 mol) are dissolved in tetrahydrofuran (100 mL) to give a clear solution. Tripentylamine (4.73 g, 0.0208 mol) is added and this colourless solution is heated to reflux and held for 3 hours at reflux (67-68° C.). Tetrahydrofuran is removed by distillation and the resulting clear, viscous oil is allowed to solidify on standing. Diethyl ether (25 mL) is added to the solid mass and the solid is filtered and washed with 3×25 mL diethyl ether, dried to a yield of 14.8 g (90.5%) I7 as a white solid. Elemental analysis. Found C, 74.86; H, 7.57; N, 1.65. Calculated for $C_{49}H_{59}NO_6Si$:C, 74.87; H, 7.57; N, 1.78.

Example 2

Preparation of I3

Benzilic acid (13.7 g, 0.06 mol) and tetraethylorthosilicate (4.17 g, 0.02 mol) are dissolved in tetrahydrofuran (75 mL). Triethylamine (5.73 g, 0.04 mol) is added and the mixture is heated to reflux (67° C.) and held at this temperature for 3 hours. Tetrahydrofuran is removed by distillation to leave a yellow oil, which is repeatedly washed with diethyl ether until crystallisation occurs. The solid is filtered from diethyl ether, washed and dried to yield 11.3 g (56.8%) of I13.

Example 3

Preparation of I8

Benzilic acid (13.7 g, 0.06 mol) and phenyltriethoxysilane (7.21 g, 0.03 mol) are dissolved in tetrahydrofuran (75 mL).

Triallylamine (4.12 g, 0.03 mol) is added and the mixture is heated to reflux (67° C.) and held at this temperature for 3 hours. Tetrahydrofuran is removed by distillation to leave a yellow solid. Diethyl ether (50 mL) is added to the solid mass and filtered. Solid is slurried in a further Diethyl ether (50 mL) at 35° C. for 10 minutes, filtered and displaced with diethyl ether. Pale yellow solid is dried to yield 19.2 g (92%) I8.

Example 4

Preparation of I47

Mandelic acid (15.2 g, 0.1 mol) and boric acid (3.1 g, 0.05 mol), are dissolved in methanol (25 mL) and water (25 mL) at room temperature. To this solution is added, a solution of triallylamine (6.86 g, 0.05 mol) in methanol (20 mL). The resulting solution is stirred at room temperature overnight. Methanol/Water is removed by distillation and the resulting residue is dissolved in ethyl acetate (50 mL). Water (50 mL) is added and subsequently separated. The upper ethyl acetate layer is dried over magnesium sulphate and distilled to dryness to leave a viscous orange oil. This orange oil is subsequently titurated with diethyl ether to yield an off-white solid which is filtered and washed with diethyl ether. The solid is dried to yield 17.5 g (77.9%) I47.

Example 5

Preparation of I45

Benzilic acid (11.41 g, 0.05 mol) and boric acid (1.54 g, 0.025 mol) are dissolved in methanol (20 mL) and water (15 mL). To this solution is added, tri-n-butylamine (4.63 g, 0.025 mol) and the mixture is stirred for 5 hours at room temperature. Water (100 mL) is added and stirred for 1 hour. The resulting solid precipitate is filtered, washed with water and dried to give a yield of 17.3 g of I45.

Example 6

Preparation of I46

Benzilic acid (11.41 g, 0.05 mol) and boric acid (1.54 g, 0.025 mol) are dissolved in methanol (20 mL) and water (15 mL). To this solution is added a solution of bis(2-ethylhexyl)amine (6.03 g, 0.025 mol) in methanol (20 mL) and stirred for 5 hours at room temperature. Water (100 mL) is added and stirred for 1 hour. The resulting solid precipitate is filtered, washed with water and dried to give a yield of 17.2 g (97.5%) of I46.

Example 7

Preparation of I37

Salicylic acid (13.8 g, 0.1 mol) and boric acid (3.1 g, 0.05 mol) are dissolved in methanol (25 mL) and water (25 mL). To this is added a solution of tripentylamine (11.4 g, 0.05 mol) in methanol (25 mL) and water (10 mL) and stirred for 24 hours at room temperature. The solvent is then reduced under vacuum. The product is extracted from the resulting residue with diethyl ether (200 mL), washed with brine and dried to yield 30.8 g (83%) of I37.

Example 8

Preparation of a Coating Composition Comprising the Amine Salt of the Organic Boron Compound I45 and Crystal Violet Lactone as Colour Former The coating composition was prepared by dissolving 0.42 g of the amine salt of the organic boron compound I45, prepared as described in example 5, in acetone (3.61 g). Crystal violet lactone (0.42 g), sold for example as Ciba® Pergascript® Blue I-2RN, is then added to the mixture followed by poly(methyl methacrylate) (1.44 g). The mixture is then further diluted by the addition of methyl ethyl ketone (7.39 g). The coating formulation is then applied by a standard coating bar method onto the substrate (paper or plastic) and imaged using a $CO_2$ IR laser to give a blue image.

Example 9

Preparation of a Coating Composition Comprising the Amine Salt of the Organic Silicon Compound I7 and Ciba® Pergascript® Orange I-G as Colour Former The coating composition was prepared by dissolving 0.42 g of the amine salt of the organic boron compound I7, prepared as described in example 1, in acetone (3.61 g). 3-Diethyl-amino-7-(ethoxycarbonyl)-fluoran (as sold for example under the tradename Ciba® Pergascript® Orange IG) (0.42 g) is then added to the mixture followed by poly(methyl methacrylate) (1.44 g). When poly(methyl methacrylate) has dissolved, 2-hydroxy-4-methoxy benzophenone (0.24 g) is then added. The mixture is then further diluted by the addition of methyl ethyl ketone (7.39 g). The coating formulation is then applied by a standard coating bar method onto the substrate (paper or plastic) to yield a transparent coating and imaged using a $CO_2$ IR laser to give an orange image.

Example 11

Preparation of a Coating Composition Comprising the Amine Salt of the Organic Boron Compound I37 and Ciba® Pergascript® Black I-2R as Colour Former The coating composition was prepared by dissolving 0.42 g of the amine salt of the organic boron compound I37, prepared as described in example 7, in acetone (3.61 g). 3-Dibutyl-amino-6-methyl-7-anilinofluoran (as sold for example under the tradename Ciba® Pergascript® Black I-2R) (0.42 g) is then added to the mixture followed by poly(methyl methacrylate). When the poly(methyl methacrylate) has dissolved, 2-hydroxy-4-methoxy benzophenone (0.24 g) is then added. The mixture is then further diluted by the addition of methyl ethyl ketone (7.39 g). The coating formulation is then applied by a standard coating bar method onto the substrate (paper or plastic) to yield a transparent coating and imaged using a $CO_2$ IR laser to give a black image.

Example 12

Preparation of a Coating Composition Comprising the Amine Salt of the Organic Boron Compound I37 and Ciba® Pergascript® Red I-6B as Colour Former The coating composition was prepared by dissolving 0.42 g of the amine salt of the organic boron compound I37, prepared as described in example 7, in acetone (3.61 g). 3,3-Bis-(1-octyl-2-methylindol-3-yl)phthalide (sold for example under the tradename Ciba® Pergascript® Red I-6B) (0.42 g) is then added to the mixture followed by poly(methyl methacrylate). When the poly(methyl methacrylate) has dissolved, 2-hydroxy-4-methoxy benzophenone (0.24 g) is then added. The mixture is then further diluted by the addition of methyl ethyl ketone (7.39 g). The coating formulation is then applied by a standard coating bar method onto the substrate (paper or plastic) and imaged using a $CO_2$ IR laser to give an orange image. The coating formulation is then applied by a standard coating bar method onto the substrate (paper or plastic) to yield a transparent coating and imaged using a $CO_2$ IR laser to give a red image.

Example 13

Preparation of a Coating Composition Comprising the Amine Salt of the Organic Silicon Compound I7 and Crystal Violet Lactone as Colour Former The coating composition was prepared by dissolving 0.42 g of the amine salt of the organic boron compound I7, prepared as described in example 1, in acetone (3.61 g). Crystal violet lactone, sold for example under the trade name Ciba® Pergascript® Blue I-2RN, (0.42 g) is then added to the mixture followed by poly(methyl methacrylate) (1.44 g). When poly(methyl methacrylate) has dissolved, an alkylated triphenyl phosphorothionate, as sold for example under the trade name Ciba® Irgalube® 211, (0.42 g) is then added. The mixture is then further diluted by the addition of methyl ethyl ketone (7.39 g). The coating formulation is then applied by a standard coating bar method onto the substrate (paper or plastic) to yield a transparent coating and imaged using a $CO_2$ IR laser to give blue image.

The invention claimed is:

1. A coating composition comprising a colour former, an amine salt of an organic metal compound, a binder, a solvent, and optionally additional components, wherein the amine salt of the organic metal compound is of formula

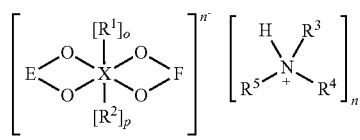

(I)

in which X is silicon or boron, and

E and F are the same or different and are selected from the group consisting of

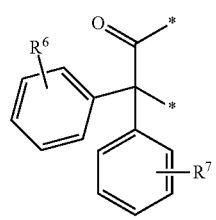 a

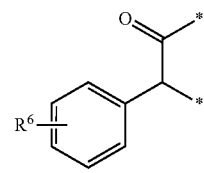 b

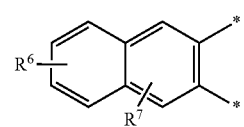 c

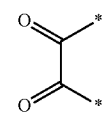 d

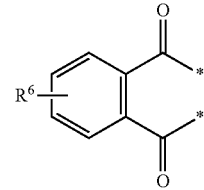 e

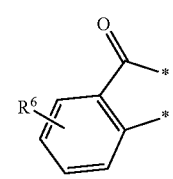 f

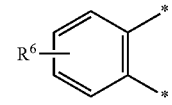 g

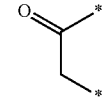 h in which $R^6$ and $R^7$ are the same or different are hydrogen, $C_{1-4}$-alkyl, $C_{1-4}$-alkoxy, halogen, amino or carboxy, and for X=silicon o=1 and p=0, and $R^1$ is aryl, aralkyl or $C_{1-4}$-alkyl, or o=1 and p=1, and $R^1$ and $R^2$ together form a one residue selected from the group consisting of a, b, c, d, e, f, g and h, and for X=boron o=0 and p=0, and $R^3$, $R^4$ and $R^5$ are the same or different and are hydrogen, $C_{1-12}$-alkyl, $C_{1-6}$-hydroxyalkyl, allyl, aralkyl or arylsulfonyl, in which aralkyl or arylsulfonyl can be substituted with $C_{1-4}$-alkyl, or $R^3$ and $R^4$ together with the nitrogen to which they are attached form a morpholino or piperidino ring.

2. The composition of claim 1, in which X is silicon, E and F are the same or different and are selected from the group consisting of

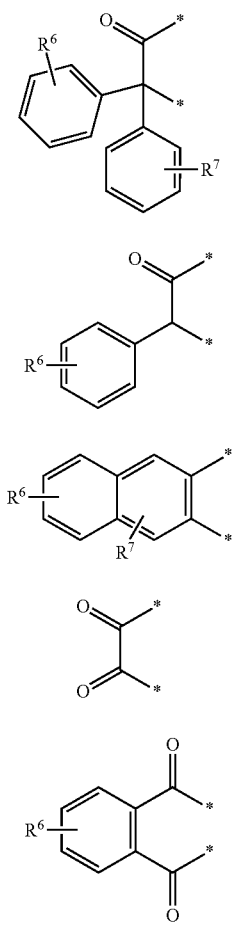

in which $R^6$ and $R^7$ are the same or different are hydrogen, $C_{1-4}$-alkyl, $C_{1-4}$-alkoxy, halogen, amino or carboxy, and o=1 and p=0, and $R^1$ is aryl, aralkyl or $C_{1-4}$-alkyl, or o=1 and p=1, and R.sup.1 and $R^2$ together form one residue selected from the group consisting of a, b, c, d and e, and $R^3$, $R^4$ and $R^5$ are the same or different and are hydrogen, $C_{1-12}$-alkyl, $C_{1-6}$-hydroxyalkyl, allyl, aralkyl or arylsulfonyl, in which aralkyl or arylsulfonyl can be substituted with $C_{1-4}$-alkyl, or $R^3$ and $R^4$ together with the nitrogen to which they are attached form a morpholino or piperidino ring.

3. The composition of claim 1, in which X is boron, E and F are the same or different and are selected from the group consisting of

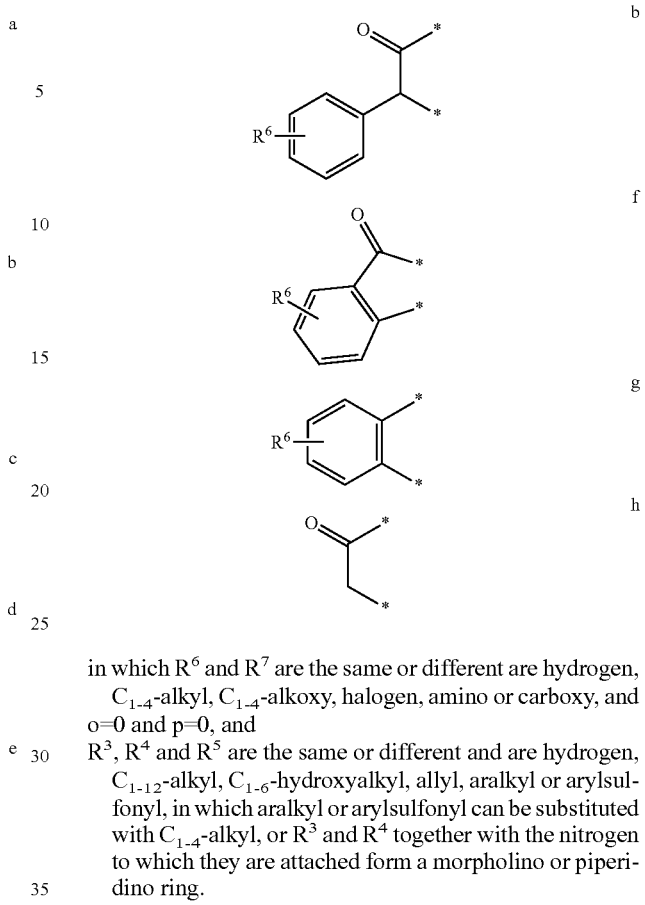

in which $R^6$ and $R^7$ are the same or different are hydrogen, $C_{1-4}$-alkyl, $C_{1-4}$-alkoxy, halogen, amino or carboxy, and o=0 and p=0, and $R^3$, $R^4$ and $R^5$ are the same or different and are hydrogen, $C_{1-12}$-alkyl, $C_{1-6}$-hydroxyalkyl, allyl, aralkyl or arylsulfonyl, in which aralkyl or arylsulfonyl can be substituted with $C_{1-4}$-alkyl, or $R^3$ and $R^4$ together with the nitrogen to which they are attached form a morpholino or piperidino ring.

4. The composition of claim 1, wherein the compositions consists of the colour former in an amount of from 0.01 to 50%, the amine salt of the organic metal compound of formula I in an amount of from 0.01 to 50%, the binder in an amount of from 1 to 80%, the solvent in an amount of from 1 to 99%, and optional additional components in an amount of from 0 to 20%, wherein each amount is by weight based on the weight of the composition.

5. The composition of claim 1 wherein the colour former is selected from the group consisting of phthalides, fluorans, triarylmethanes, benzoxazines, quinazolines, spiropyrans, quinones, thiazines, oxazines and mixtures thereof.

6. The composition of claim 1 wherein the binder is a polymeric binder.

7. The composition o claim 1, wherein the solvent is selected from the group consisting of organic solvents, mixtures of organic solvents, and mixtures of one or more organic solvent(s) with water.

8. The composition of claim 1, wherein the composition is either a solution or dispersion.

9. The composition of claim 8, wherein the composition is a solution.

10. A process for preparing the composition of claim 1 comprising the step of mixing the amine salt of the organic metal compound I, the colour developer, the binder, optionally additional components and the solvent.

11. A substrate coated with the composition of claim 1.

12. A process for preparing a substrate coated with the composition of claim 1, comprising the step of i) coating a substrate with the composition of claim 1.

13. A process for preparing a marked substrate comprising the steps of i) coating a substrate with the composition of

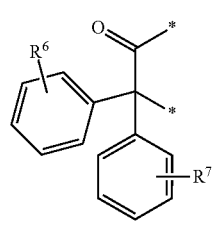

claim 1, and ii) exposing those parts of the coated substrate, where a marking is intended, to energy in order to generate a colour marking.

14. The process of claim 13, wherein the energy is IR irradiation.

15. A marked substrate obtained by the process of claim 14.

16. A marked substrate obtained by the process of claim 13.

* * * * *